United States Patent

Kirsch et al.

[11] Patent Number: 5,089,007
[45] Date of Patent: Feb. 18, 1992

[54] MULTIPURPOSE SURGICAL TOOL

[75] Inventors: Wolff M. Kirsch, Redlands, Calif.; Yong H. Zhu; Robert B. Cushman, Cedar Crest, both of N. Mex.

[73] Assignee: The University of New Mexico, Albuquerque, N. Mex.

[21] Appl. No.: 479,567

[22] Filed: Feb. 14, 1990

[51] Int. Cl.⁵ .............................................. A61B 17/28
[52] U.S. Cl. .................... 606/205; 606/210; 294/99.2
[58] Field of Search .............. 606/205, 206, 207, 208, 606/209, 210, 211, 142, 139; 81/38; 294/99.1, 99.2, 100

[56] References Cited

U.S. PATENT DOCUMENTS

| | | |
|---|---|---|
| 1,615,125 | 1/1927 | Lesipasse . |
| 3,774,438 | 11/1973 | Weston . |
| 3,805,792 | 4/1974 | Cogley . |
| 3,827,277 | 8/1974 | Weston . |
| 4,165,745 | 8/1979 | Heifetz . |
| 4,212,305 | 7/1980 | Lahay . |
| 4,394,864 | 7/1983 | Sandhaus . |
| 4,491,135 | 1/1985 | Klein . |
| 4,592,347 | 6/1986 | Mahruki . |
| 4,693,246 | 9/1987 | Reimels . |

FOREIGN PATENT DOCUMENTS 0902641  9/1945  France ................. 606/210

Primary Examiner—C. Fred Rosenbaum
Assistant Examiner—William Lewis
Attorney, Agent, or Firm—Hoffman, Wasson & Gitler

[57] ABSTRACT

A surgical tool for cutting, shearing or clamping has a body formed of a single length of flexible steel and a collet mounted perpendicularly between the leaves of the body and affixed between the leaves near their rearward ends. The leaves are normally bowed outward, so that squeezing them together lengthens the body, thus producing relative displacement between the forward ends of the body and collet, respectively. The bifurcated forward end of the collet, which extends through an aperture in a bridge joining the leaves, terminates at a pair of jaws having inwardly working surfaces and outwardly facing cam surfaces. The cams are engaged by the sides of the aperture, which drive the jaws together when the leaves are squeezed toward one another.

21 Claims, 1 Drawing Sheet

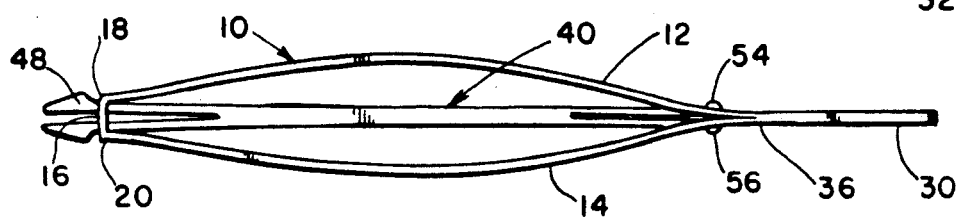
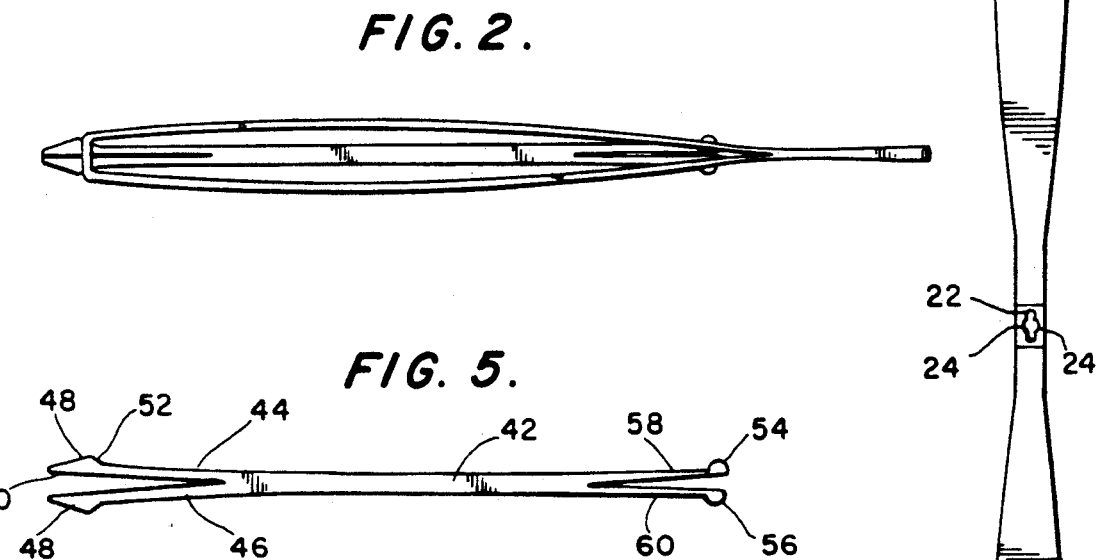
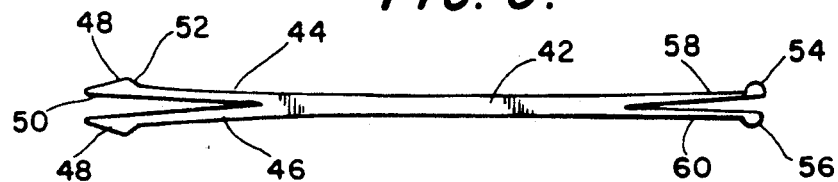
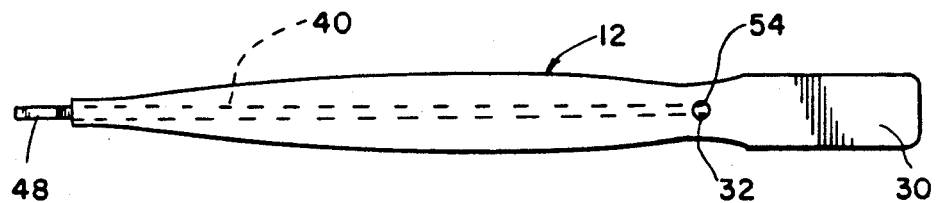
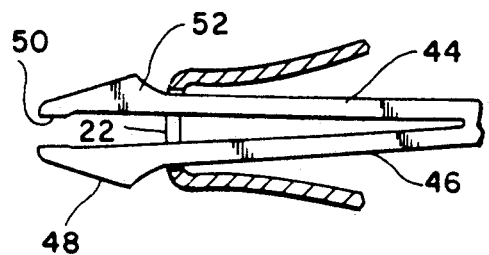

MULTIPURPOSE SURGICAL TOOL

BACKGROUND

This invention relates generally to the field of surgery and more particularly to a hand tool capable of performing cutting, clamping, or shearing functions in surgical operations.

In surgery, there is a frequent need to cut, clamp or shear tissues and other materials of small size. A variety of tools have been developed to perform such functions. Prior devices, however, tend to be unnecessarily complex and thus relatively expensive and difficult to clean properly.

Forceps and tweezers typically have a pair of handles interconnected by a pivot or flexible connection at a point along their length, so that squeezing the handles together produces relative jaw movement. The handles usually are substantially rigid, as in U.S. Pat. No. 4,693,246; however, thin-section handles designed to flex when pressure is applied, in order to move the jaws, have been proposed also, as in U.S. Pat. Nos. 4,212,305, No. 3,805,792. No. 1,615,125, No. 3,827,277 and No. 2,774,438.

The jaws of tweezers or forceps are usually integral extensions of the handles; however, some prior devices have separate jaws which are closed by withdrawing the jaws or a jaw assembly into a tube or the like. Examples of such devices are found in U.S. Pat. Nos. 4,592,347 and 4,394,864, and in U.S. Pat. Nos. 2,827,277 and 3,774,438, above. The latter two patents are made of plastic, so that they can be thrown away after use.

SUMMARY OF THE INVENTION

It is an object of the present invention to provide a tool of simple manufacture.

A further object of the invention is to provide a lightweight tool capable of performing cutting, clamping or shearing functions, depending upon the shape of the jaws.

Another object is to enable a surgeon to cut, clamp or shear material simply by squeezing the sides of the tool together.

It is also an object of the invention to provide a tool which can be easily disassembled, cleaned and reassembled.

One further object is to assist a surgeon in regulating the degree of closure of jaws of such a tool by providing tactile feedback in the form of increasing resistance to the hand as a function of jaw closure.

The invention is embodied in a tool intended particularly for surgery, comprising a body portion including a pair of flexible leaves joined at their forward ends by a bridge having an aperture therein, and joined face-to-face at their rearward ends. An elongated collet extending perpendicularly between the leaves of the body is retained between the leaves at its rearward end. The leaves, normally bowed outward from one another, can be squeezed toward one another, so as to lengthen the body and produce relative movement between the bridge and the forward end of the collet. A pair of tines at the forward end of the collet have inwardly facing working edges or jaws and outwardly facing oblique cam surfaces which interact with opposite sides of the aperture, to close the jaws, when the bridge portion of the body is driven toward the jaws by squeezing the leaves.

BRIEF DESCRIPTION OF THE DRAWINGS

In the accompanying drawings,

FIGS. 1 and 2 are front views showing open and closed positions of a multipurpose surgical tool embodying the invention;

FIG. 3 is top view of the tool shown in FIG. 1;

FIG. 4 is a detail view of a blank from which the body of the tool is formed;

FIG. 5 is a detail view of jawed collet shown in FIG. 1; and

FIG. 6 is a detail showing the jaws and distal end of the tool body in detail.

DESCRIPTION OF THE PREFERRED EMBODIMENT

A surgical tool embodying the invention, shown in FIGS. 1-3, comprises only two parts—a body portion 10 and a collet 40, both constructed from a resilient sheet metal such as stainless steel. The gauge of the material is chosen so as to provide sufficient flexibility that plastic deformation of the tool does not occur in normal use (hence the term "resiliently flexible" hereafter), and to provide the desired spring rate, according to the intended use of the tool.

The body portion 10 includes a pair of identical leaves 12, 14 extending from opposite sides of a bight or bridge 16 defined by folding the blank on lines 18, 20. The bridge has a preformed aperture 22 at its center (see the body layout or blank, before folding, in FIG. 4). The aperture is symmetrical about the center plane P of the tool, and has the form of an elongated slot with widened portions 24 at the center plane.

After the folds 18, 20 are made, the tabs 26, 28 at the ends of the blank are drawn together—the resilience of the leaves resulting in an outwardly bowed configuration as shown—and are welded or otherwise joined together to form a handle 30. The handle end of the tool is referred to as the "rearward" end of the tool hereafter. Aligned holes 32, 34 extend through the leaves near the tab juncture 36.

The collet 40, shown in detail in FIG. 5, comprises an elongate bar 42 which is bifurcated at both ends to form resiliently flexible forward tines 44, 46 and rearward tines 58, 60. Each of the forward tines has a jaw 48 at the distal end thereof. Each jaw (FIG. 6) has an inner working face or edge 50 and an outer edge, a portion of which obliquely angled so as to define a cam surface 52. The cam surfaces are preferably planar, and if extended would meet at the center plane of the tools, subtending an acute angle alpha as shown.

The tines 44, 46 are resiliently flexible, so that the jaws can be deflected inwardly to the point where their working edges 50 meet (FIG. 2), and then return to their original open position when released (FIG. 1). Preferably, the tines, jaws and aperture are designed so that the tines are slightly flexed even in the relaxed position of the tool, whereby the cam surfaces are always in contact with the sides of the aperture.

The collet 40 is permanently retained between the leaves of the body by tabs 54, 56 which extend outward from the ends of rearward tines 58, 60. In the assembled position, the tines 58, 60 are deflected inward from their free position, so as to maintain a constant outward bias on the tabs 54, 56, and thus eliminate any free motion of the collet. It is apparent that the collet is aligned, by the aperture and by the holes 32, 34, so that a plane containing the four tines is perpendicular to and bisects each of the leaves. That is, the width of the collet is perpendicular to the leaves.

The arrangement of tabs 54, 56, tines 58, 60 and holes 32, 34 is preferred because it provides for easy tool assembly and disassembly. However, the rearward end of the collet may be affixed between the leaves 12, 14, by other means, as long as such means perform the function of preventing substantial relative movement between the rearward ends of the parts.

In use, with the jaws astride a workpiece or tissue, the leaves are squeezed together, changing their free, bowed configuration (FIG. 1) to a more linear configuration (FIG. 2). The straightening of the leaves lengthens the body slightly. Since the body and collet are interconnected at their rearward ends, the effect of this lengthening is to withdraw the jaws into the aperture, or actually, to displace the bridge portion of the body forward with respect to the jaws. As this occurs, interaction between the oblique cam surfaces and the sides of the aperture forces the jaws toward one another, against both the spring bias provided by the tines and any resistance of work material between the jaws. When inward pressure on the leaves is removed, their resilience restores the body to its original length, and the jaws, no longer constrained by the sides of the aperture, spring back to their original position.

Because both of the tool components can be stamped from sheet metal, their manufacture is very straightforward and inexpensive; in addition, it is a simple matter to snap the two parts of the tool together. The tool is easily and thoroughly cleaned and sterilized, having no pivot points or recesses to harbor contaminants.

While the foregoing describes use of the tool in the field of surgery, the tool may find appropriate uses in other applications requiring a small, simple jawed tool.

Inasmuch as the invention is subject to numerous variations and changes in detail, the foregoing description, and the accompanying drawings, should be understood as merely illustrative of the invention defined by the following claims.

We claim:

1. A tool comprising:
   a body portion comprising a pair of resiliently flexible leaves joined at their forward ends by a bridge having an aperture therein, said leaves also being joined face-toface at their rearward ends, and being normally bowed outward from one another; and
   an elongated collet having a rearward end affixed to the rearward ends of said leaves, and a bifurcated forward end comprising a pair of resiliently flexible tines, each tine having thereon a jaw protruding through said aperture, each jaw including an inwardly facing working surface and an outwardly facing oblique cam surface in a position to engage a side of said aperture, so that relative longitudinal movement between the bridge and the jaws, produced by squeezing the leaves together, causes interaction between the sides of the aperture and the cam surfaces to drive the jaws together, wherein said aperture has the form of a slot, widened at its center.

2. The invention of claim 1, wherein said aperture has the form of a slot, widened at its center.

3. The invention of claim 1, wherein said leaves have respective through holes at their rearward ends, and wherein said affixing means comprises a second pair of tines, at the rearward end of said collect, each of said second pair of tines having an outwardly protruding tab for engagement within a respective one of said holes.

4. The invention of claim 3, wherein said second pair of tines are flexed inwardly by contact with the leaves as long as the collet is assembled within the body.

5. The invention of claim 1, wherein said first pair of tines are flexed inwardly by the sides of the aperture as long as the collet is assembled within the body.

6. The invention of claim 1, wherein the tines of the collet lie in a common plane perpendicular to and bisecting both of said leaves, the length of the slot being aligned with said plane.

7. The invention of claim 1, wherein the body is bent from a sheet metal blank having the aperture preformed therein, by bending the blank on either side of the aperture to define said bridge.

8. A method of making the tool of claim 1, comprising steps
   forming a sheet metal blank including a pair of identical leaves interconnected by an integral bridge portion,
   forming an aperture through said bridge portion,
   forming a hole through each of said leaves near the free ends thereof, said holes being equidistant from said bridge portion,
   folding said leaves in a common direction from said bridge portion,
   interconnecting the free ends of said leaves face-to-face to form a handle, and
   inserting a collet having a resilient rearward tine with protuberances thereon through said aperture, so that said protuberances snap into said holes to retain the collet between said leaves.

9. A tool comprising:
   a body portion comprising a pair of resiliently flexible leaves joined at their forward ends by a bridge having an aperture therein, said leaves also being joined face-to-face at their rearward ends, and being normally bowed outward from one another; and
   an elongated collet having a rearward end affixed to the rearward ends of said leaves, and a bifurcated forward end comprising a first pair of resiliently flexible tines, each tine having thereon a jaw protruding through said aperture, each jaw including an inwardly facing working surface and an outwardly facing oblique cam surface in a position to engage a side of said aperture, so that relative longitudinal movement between the bridge and the jaws, produced by squeezing the leaves together, causes interaction between the sides of the aperture and the cam surfaces to drive the jaws together,
   wherein said leaves have respective through holes at their rearward ends, and wherein said affixing means comprises a second pair of tines, at the rearward end of said collet, each of said second pair of tines having an outwardly protruding tab for engagement within a respective one of said holes.

10. The invention of claim 9, wherein said second pair of tines are flexed inwardly by contact with the leaves as long as the collet is assembled within the body.

11. A tool comprising:
   a body portion comprising a pair of resiliently flexible leaves joined at their forward ends by a bridge having an aperture therein, said leaves also being joined face-to-face at their rearward ends, and being normally bowed outward from one another; and an elongated collet having a rearward end affixed to the rearward ends of said leaves, and a bifurcated forward end comprising a pair of resiliently flexible tines, each tine having thereon a jaw protruding through said aperture, each jaw including an inwardly facing working surface and an outwardly facing oblique cam surface in a position to engage a side of said aperture, so that relative longitudinal movement between the bridge and the jaws, produced by squeezing the leaves together, causes interaction between the sides of the aperture and the cam surfaces to drive the jaws together wherein the tines of the collet lie in a common plane perpendicular to and bisecting both of said leaves, the length of the slot being aligned with said plane.

12. A tool comprising:

a body portion comprising a pair of resiliently flexible leaves joined at their forward ends by a bridge having an aperture therein, said leaves also being joined face-to-face at their rearward ends, and being normally bowed outward from one another; and an elongated collet having a rearward end affixed to the rearward ends of said leaves, and a bifurcated forward end comprising a pair of resiliently flexible tines, each tine having thereon a jaw protruding through said aperture, each jaw including an inwardly facing working surface and an outwardly facing oblique cam surface in a position to engage a side of said aperture, so that relatively longitudinal movement between the bridge and the jaws, produced by squeezing the leaves together, causes interaction between the sides of the aperture and the cam surfaces to drive the jaws together, wherein the body is bent from a sheet metal blank having the aperture preformed therein, by bending the blank on either side of the aperture to define said bridge.

13. A method of making a tool comprising:

a body portion comprising a pair of resiliently flexible leaves joined at their forward ends by a bridge having an aperture therein, said leaves also being joined face-to-face at their rearward ends, and being normally bowed outward from one another; and an elongated collet having a rearward end affixed to the rearward ends of said leaves, and a bifurcated forward end comprising a pair of resiliently flexible tines, each tine having thereon a jaw protruding through said aperture, each jaw including an inwardly facing working surface and an outwardly facing oblique cam surface in a position to engage a side of said aperture, so that relative longitudinal movement between the bridge and the jaws, produced by squeezing the leaves together, causes interaction between the sides of the aperture and the cam surfaces to drive the jaws together, comprising the steps of:

forming a sheet metal blank including a pair of identical leaves interconnected by an integral bridge portion, forming an aperture through said bridge portion, forming a hole through each of said leaves near the free ends thereof, said holes being equidistant from said bridge portion, folding said leaves in common direction from said bridge portion, interconnecting the free ends of said leaves face-to-face to form a handle, and inserting a collet having a resilient rearward tine with protuberances thereon through said aperture, so that said protuberances snap into said holes to retain the collet between said leaves.

14. A tool comprising:

a body portion comprising a pair of resiliently flexible leaves in a plane joined at their forward ends by a bridge having an aperture therein, said leaves also being joined face-to-face at their rearward ends, and being normally bowed outward from one another; and an elongated collet having a rearward end affixed to the rearward ends of said leaves, and a bifurcated forward end comprising a first pair of resiliently flexible tines in the same plane as said leaves, each tine having thereon a jaw protruding through said aperture, each jaw including an inwardly facing working surface and an outwardly facing oblique cam surface in a position to engage a side of said aperture, so that relative longitudinal movement between the bridge and the jaws, produced by squeezing the leaves together, causes interaction between the sides of the aperture and the cam surfaces to drive the jaws together.

15. The invention of claim 14, wherein said aperture has the form of a slot, widened at its center.

16. The invention of claim 14, wherein said leaves have respective through holes at their rearward ends, and wherein said affixing means comprises a second pair of tines, at the rearward end of said collet each of said second pair of tines having an outwardly protruding tab for engagement within a respective one of said holes.

17. The invention of claim 16, wherein said second pair of tines are flexed inwardly by contact with the leaves as long as the collet is assembled within the body.

18. The invention of claim 14, wherein said first pair of tines are flexed inwardly by the sides of the aperture as long as the collet is assembled within the body.

19. The invention of claim 14, wherein the tines of the collet lie in a common plane perpendicular to and bisecting both of said leaves, the length of the slot being aligned with said plane.

20. The invention of claim 14, wherein the body is bent from a sheet metal blank having the aperture preformed therein, by bending the blank on either side of the aperture to define said bridge.

21. A method of making the tool of claim 14, comprising the steps of:

forming a sheet metal blank including a pair of identical leaves interconnected by an integral bridge portion;

forming an aperture through said bridge portion;

forming a hole through each of said leaves near the free ends thereof, said holes being equidistant from said bridge portion;

folding said leaves in a common direction from said bridge portion;

interconnecting the free ends of said leaves face-to-face to form a handle; and inserting a collet having a resilient tine with protuberances thereon through said aperture, so that said protuberances snap into said holes to retain the collet between said leaves.

* * * * *